(12) United States Patent
Carter et al.

(10) Patent No.: US 6,830,052 B2
(45) Date of Patent: Dec. 14, 2004

(54) URETHRAL SUPPORT FOR INCONTINENCE

(75) Inventors: Garry L. Carter, Pleasanton, CA (US); David R. Stiehr, Pleasanton, CA (US)

(73) Assignee: Solarant Medical, Inc., Livermore, CA (US)

(*) Notice: Subject to any disclaimer, the term of this patent is extended or adjusted under 35 U.S.C. 154(b) by 0 days.

(21) Appl. No.: 09/971,051

(22) Filed: Oct. 3, 2001

(65) Prior Publication Data
US 2003/0062052 A1 Apr. 3, 2003

(51) Int. Cl.[7] .................................................. A61F 5/48
(52) U.S. Cl. ................... 128/885; 600/29; 128/DIG. 25
(58) Field of Search ................................. 128/846, 885, 128/886, DIG. 25; 600/29–31

(56) References Cited

U.S. PATENT DOCUMENTS

| | | | |
|---|---|---|---|
| 5,123,428 A | 6/1992 | Schwarz | |
| 5,337,736 A | 8/1994 | Reddy | |
| 5,618,257 A | 4/1997 | Kulisz et al. | |
| 5,637,074 A * | 6/1997 | Andino | 600/29 |
| 5,816,258 A * | 10/1998 | Jervis | 128/898 |
| 5,840,011 A | 11/1998 | Landgrebe et al. | |
| 5,846,180 A | 12/1998 | Kulisz et al. | |
| 5,899,909 A | 5/1999 | Claren et al. | |
| 6,042,583 A * | 3/2000 | Thompson et al. | 606/72 |
| 2002/0143234 A1 * | 10/2002 | LoVuolo | 600/30 |

* cited by examiner

Primary Examiner—Michael A. Brown
(74) Attorney, Agent, or Firm—Townsend and Townsend and Crew LLP; Lynn M. Thompson

(57) ABSTRACT

The present invention provides methods, devices, and systems for supporting the urethra in a patient to treat urinary incontinence. Support of the urethra involves forming a loop under the urethra with a structure referred to as a urethral support and applying an upward force with the support to hold the urethra in a more desired position. The present invention utilizes the space of Retzius within which portions of the urethral support are positioned. Ingrowth by surrounding tissues to the urethral support material provide further stability and such ingrowth, combined with the position of the support, allow sufficient tension to be applied to support to hold the urethra in place. Placement of such a urethral support is achieved by minimally invasive techniques, such as with the use of laparoscopic instruments. Such techniques allows placement of the urethral support by accessing the space of Retzius through the vaginal wall without penetrating the abdominal wall. Such techniques also avoid perforations of nearby organs, such as the bladder, by utilizing specialized penetration devices.

26 Claims, 7 Drawing Sheets

URETHRAL SUPPORT FOR INCONTINENCE

BACKGROUND OF THE INVENTION

1. Field of the Invention

The present invention generally relates to methods, devices and systems for the treatment of urinary incontinence. In particular, the present invention provides methods, devices and systems for supporting the urethra in the female anatomy. More particularly, the present invention provides such treatment in a laparoscopic or a minimally invasive manner.

Urinary incontinence arises in both women and men with varying degrees of severity and from different causes. In men, the condition occurs almost exclusively as a result of prostatectomies which result in mechanical damage to the sphincter. In women, the condition typically arises after pregnancy where musculo-skeletal damage has occurred as a result of inelastic stretching of the structures which support the genitourinary tract. Specifically, pregnancy can result in inelastic stretching of the pelvic floor, the external vaginal sphincter, and most often, the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively, or additionally, patients may undertake exercises intended to strengthen the muscles in the pelvic region, or may attempt behavior modification intended to reduce the incidence of urinary leakage. In cases where such noninterventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are sometimes looped around the bladder neck and affixed to the pelvis, the endopelvic fascia, the ligaments which support the bladder, or the like. In other cases, the structures are extended over the pubis and through the abdominal wall. The ends of the structure are then available outside the abdominal wall where they may be tightened and fixed for permanent implantation. Other procedures involve surgical injections of bulking agents, inflatable balloons, or other elements to mechanically support the bladder neck.

Each of these procedures has associated shortcomings. Surgical operations which involve suturing of the tissue structures supporting the urethra or bladder neck region require great skill and care to achieve the proper level of artificial support. In other words, it is necessary to occlude the urethra or support the tissues sufficiently to inhibit urinary leakage, but not so much that normal intentional voiding of urine is made difficult or impossible. Balloons and other bulking agents which have been inserted can migrate or be absorbed by the body. The presence of such inserts can also be a source of urinary tract infections.

For these reasons, it would be desirable to provide improved methods, devices and systems for treating urinary incontinence. In particular, it would be desirable to provide such treatment in a minimally invasive manner, preferably utilizing laparoscopic or a least invasive manner to minimize patient trauma. It would further be desirable to provide treatment methods which reduce the potential to perforate the bladder and avoid puncturing the abdominal wall. It would also be desirable to provide methods and devices which avoid the potential drawbacks of bone anchors, such as infection and osteitis pubis. At least some of these objectives will be met by the methods, devices and systems of the present invention described hereinafter.

2. Description of the Background Art

A method for implanting an artificial sphincter to control urinary incontinence is described in U.S. Pat. No. 5,123,428. The first procedure employs a trocar or laparoscope to insert and position an inflatable balloon in the patient's space of Retzius. The patient's anterior bladder is connected to the patient's abdominal wall by a patch to effectively lengthen and stabilize the urethra. The second procedure is to implant a fluid reservoir and manually-actuable valve subcutaneously and connect them to the balloon in a closed system.

A sling having a web for moving an organ or vessel, and sutures connected to the web for maintaining the organ in its displaced position, are described in U.S. Pat. No. 5,337,736. An implant for suspension of the urinary bladder is described in U.S. Pat. No. 5,840,011.

An insertion apparatus for a female bladder control device is described in U.S. Pat. Nos. 5,618,257 and 5,846,180. The insertion apparatus includes an outer tube for insertion into the urethra of a patient, the outer tube having a retention collar for limiting the depth of insertion of the outer tube.

A surgical instrument and a method for treating female urinary incontinence is described in U.S. Pat. No. 5,899,909. When practicing the method the instrument is manipulated so as to position a tape to form a loop around the urethra. The tape is extended over the pubis and through the abdominal wall where it is tightened. Then, the tape ends are cut at the abdominal wall and the tape is left implanted in the body.

BRIEF SUMMARY OF THE INVENTION

The present invention provides methods, devices, and systems for supporting the urethra in a patient to treat urinary incontinence. Support of the urethra involves forming a loop under the urethra with a structure referred to as a urethral support and applying an upward force with the support to hold the urethra in a more desired position. Such a force may be achieved by securely positioning portions of the urethral support within the abdominal anatomy and applying tension to such portions to support the urethra. The present invention utilizes the space of Retzius within which portions of the urethral support are positioned. Ingrowth by surrounding tissues to the urethral support material provide further stability and such ingrowth, combined with the position of the support, allows sufficient tension to be applied to the support to hold the urethra in place. Placement of such a urethral support is achieved by minimally invasive techniques, such as with the use of laparoscopic instruments. Such techniques allow placement of the urethral support by accessing the space of Retzius through the vaginal wall without penetrating the abdominal wall. Such techniques also avoid perforations of nearby organs, such as the bladder, by utilizing specialized penetration devices.

In one aspect of the present invention, a passageway is created within the abdominal anatomy through which at least a portion of the urethral support is advanced and positioned for implantation. Such a passageway is created to extend from the vagina, through the vaginal wall and body tissue or fat layers, to the space of Retzius generally located between the bladder and the pubic bone. By accessing the space of Retzius through the vagina rather than through the abdominal wall, the procedure is less invasive and traumatic to the patient leaving no visible scars. However, such access requires attention to nearby organs which must be avoided to prevent perforation or damage. This may be achieved with the use of specialized penetration devices.

To begin, a penetration device is inserted through the vaginal wall, comprising an endopelvic fascia layer and a mucosal layer. In one embodiment, the penetration device comprises a Veress-style needle. As the needle is advanced beyond the vaginal wall, through body tissue and fat layers, a plunger guards the needle for atraumatic passage through fatty tissues or along tissue planes. Thus, resilient organs, such as the bladder, are pushed way from the needle by the plunger, avoiding perforation. In addition, the penetration device may include a depth stop which defines a maximum depth of penetration by the penetration device. The depth stop provides a stopping surface which rests against the vaginal wall and prevents further insertion of the needle.

The penetration device typically includes a sheath mounted on the needle so that the sheath is positioned within the passageway as it is created. Thus, the penetration device may then be withdrawn leaving the sheath behind in the passageway formed from the space of Retzius to the vagina. At this point, a blunt dilator is inserted into the sheath to dilate the passageway and a portion of the space of Retzius. The dilator is then exchanged with a delivery catheter which is used to place at least a portion of the urethral support within the space of Retzius.

In another aspect of the present invention, the urethral support comprises a number of embodiments. In one embodiment, the urethral support comprises at least one anchor patch. Typical anchor patches are rectangular in shape and are comprised of a flexible, porous material having at least one side with a frictional surface to prevent slippage between tissue layers. In addition, the anchor patch may have sutures attached, typically at one end of the patch. The anchor patch is then positioned in the passageway so that at least a portion of the patch resides with the space of Retzius and the sutures are positioned such that their free ends exit through at least the endopelvic fascia layer of the vaginal wall. Thus, the patch, including the sutures, extends through the abdominal anatomy to one side of the urethra. Generally, another anchor patch is positioned in the same manner through a second passageway on the opposite side of the urethra. Then, the free ends of the sutures are utilized to provide support under the urethra. For example, the free ends may be fastened to the vaginal wall wherein the anchor patches are adjusted to apply tension to the patches and upward force on the urethra. Alternatively, the sutures may be connected, such as by a band or similar device which is positioned under the urethra for attachment to the suture ends. Again, the anchor patches may then be adjusted to apply tension to the patches and upward force on the urethra.

In another embodiment, the urethral support comprises a sling which is used to form a loop under the urethra for support. Similar to the anchor patch, the sling may be comprised of a flexible, porous material having a frictional surface to prevent slippage. However, such a sling typically comprises two ends, each of which are implanted within the space of Retzius. One end of the sling is deployed within the passageway so that the sling extends from the space of Retzius to one side of the urethra and through the vaginal wall. The other end of the sling is positioned in the same manner through a second passageway on the opposite side of the urethra. Thus, the sling forms a loop underneath the urethra. The sling may then be adjusted to apply tension to the sling and upward force on the urethra. In any case, the portion of the urethral support positioned under the urethra may be covered by the mucosal layer to protect the implanted device and provide a seamless interface for the patient.

Other objects and advantages of the present invention will become apparent from the detailed description to follow, together with the accompanying drawings.

DETAILED DESCRIPTION OF THE INVENTION

Figure 1:
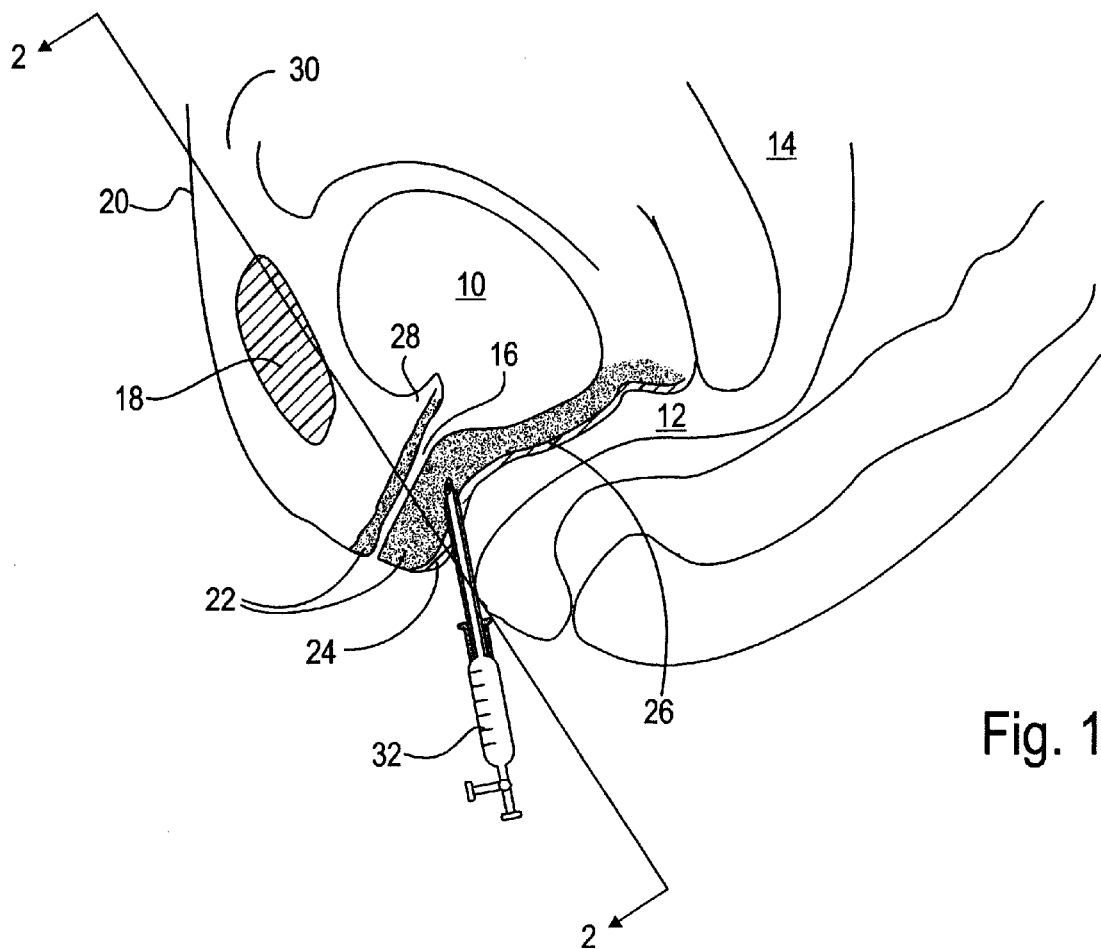
FIG. 1 is a schematic side view illustration of the relevant parts of the female abdominal anatomy and shows insertion of the penetration device through the vaginal wall.

The present invention generally provides methods, devices and systems for treating urinary incontinence, particularly in the female patient. Referring to FIG. 1 the relevant parts of the female lower anatomy is depicted diagrammatically in a side view. Identified parts include a bladder 10, a vagina 12, a uterus 14, a urethra 16, a pubic bone 18, and an abdominal wall 20. The urethra 16 is surrounded by endopelvic fascia 22, as shown. A mucosal layer 24 lines the vagina 12, wherein the mucosal layer 24 and endopelvic fascia 22 make up the vaginal wall 26. Body tissue, such as fat 28, surround portions of the bladder 10 and other anatomical parts in the abdomen. In particular, a pad of fat 28, which is several millimeters thick, resides between the endopelvic fascia 22 and the bladder 10. Tissue planes exist between the pubic bone 18 and the bladder 10 which may be separated leading to a space of Retzius 30. The space of Retzius 30 may be used as a location for implanting devices of the present invention as will be described hereinafter.

Figure 2:
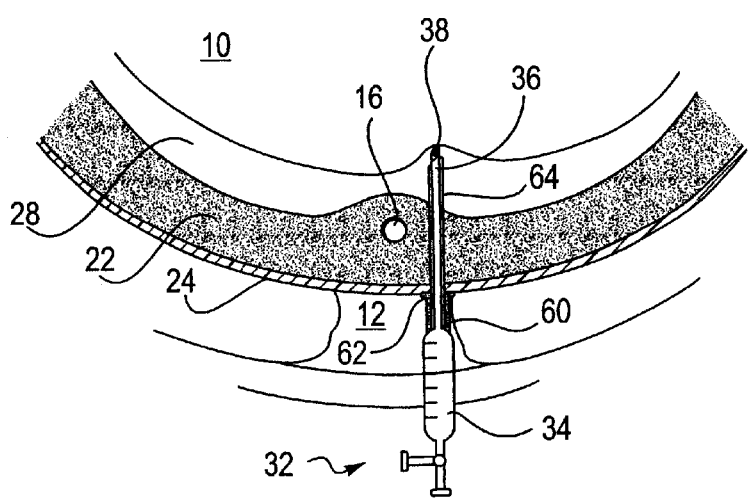
FIG. 2 is a schematic front view illustration of a Veress-style needle penetration device inserted through the body tissues to create a passageway on one side of the urethra.

Referring again to FIG. 1, methods of the present invention include creating a passageway from the vagina 12 to the space of Retzius 30. Such a passageway may be created by penetrating through the vaginal wall 26 with the use of a penetration device 32. The penetration device 32 may have any useful shape, such as straight or curved, for accessing the vaginal wall 26 through the opening to the vagina 12. FIG. 2 illustrates a cross-sectional front view of the female lower anatomy correlating to FIG. 1. Again, the penetration device 32 is inserted through the mucosal layer 24 of the vaginal wall 26. The device 32 is advanced through the endopelvic fascia 22 and portions of the fat 28 layer on one side of the urethra 16, as shown. The penetration device 32 may comprise any number of suitable embodiments for such use. In a preferred embodiment, the penetration device 32 comprises a Veress-style needle 34. Veress-style needles 34 are used in laparoscopic procedures in an effort to reduce the risk of perforating significant veins and arteries during passage of the needle. Such a needle 34 typically includes a sharpened elongate needle 36 and a spring-loaded plunger 38 which guards the needle 36 during insertion. As shown, as the Veress-style needle 34 is advanced, the plunger 38 guards the needle 36 for atraumatic passage through soft tissues. The plunger 38 maintains this position to maneuver around resilient organs, such as the bladder 10, without perforating or causing trauma to the organs. As illustrated in FIG. 2, the bladder 10 may be pushed away from the needle 34 during creation of the passageway to the space of Retzius 30. The spring-loaded plunger 38 will retract and allow penetration by the sharpened needle 36 when in contact with less resilient body tissues.

In addition, the penetration device 32 may include a depth stop 60 to allow a maximum depth of penetration by the penetration device 32. The maximum depth should allow penetration from the vagina 12 through the mucosal layer 24 and the layer of endopelvic fascia 22 but not enough to perforate the wall of the bladder 10. The nominal thickness of the endopelvic fascia 22 is typically 3–5 mm and the thickness of the surrounding fat 28 is generally in the range of 2–3 mm. Therefore the desired maximum depth of penetration is about 8 mm. The depth stop 60 may be incorporated in or fixed to the penetration device 32 providing a stopping surface 62 which rests against the vaginal wall 26 and prevents further insertion. It may be appreciated that the depth stop 60 may take a number of forms to prevent over-insertion of the penetration device 32.

Figure 3:
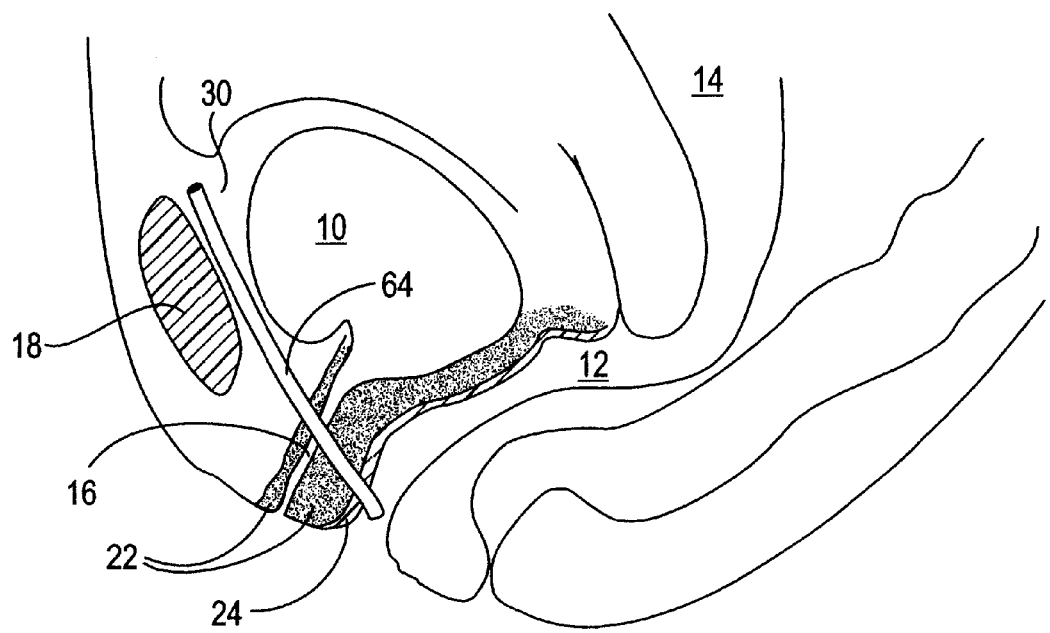
FIG. 3 illustrates the positioning of the sheath in the passageway from the space of Retzius through the vaginal wall.

A sheath 64 may also be mounted on the penetration device 32, particularly on the sharpened elongate needle 36 as shown. Thus, the sheath 64 is advanced along with the penetration device 32 as the passageway is created from the vagina 12 to the space of Retzius 30. Referring now to FIG. 3, the sheath 64 may be left behind in the passageway after the penetration device 32 is removed. The sheath 64 thus provides a pathway through which additional devices and treatment catheters may be passed.

Figure 4:
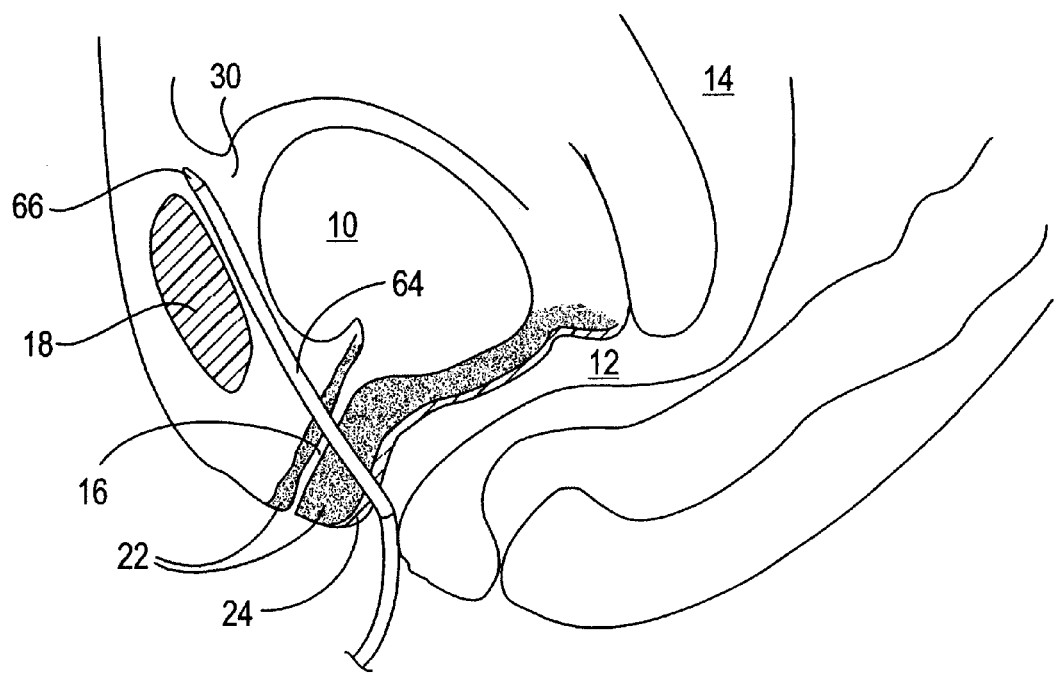
FIG. 4 illustrates the insertion of a blunt dilator into the sheath.

As shown in FIG. 4, a blunt dilator 66 is then inserted into the sheath to atraumatically dilate the passageway and access the space of Retzius 30. The dilator 66 may be appropriately curved as shown for access through the opening to the vagina 12. Since an end of the sheath 64 is disposed in the space of Retzius 30, the dilator 66 is then passed through the space of Retzius 30 for a distance of approximately 8 to 10 cm until a space is accessible between the public bone 18 and the bladder 10.

Figure 5:
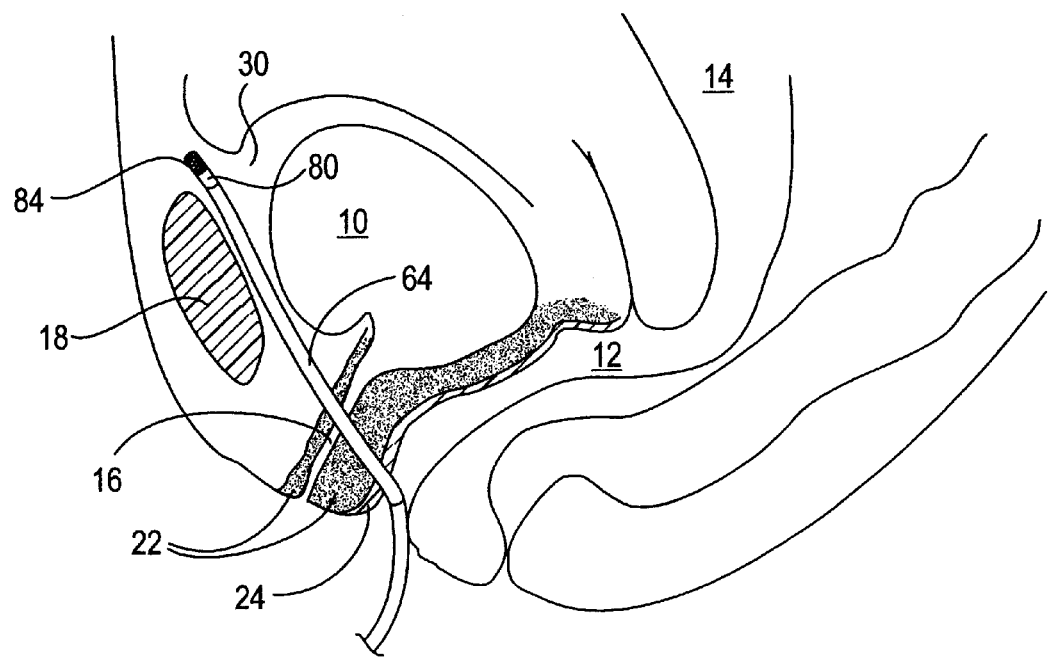
FIG. 5 illustrates the insertion of the delivery catheter into the sheath including the urethral support deployable within the space of Retzius.
Figure 6:
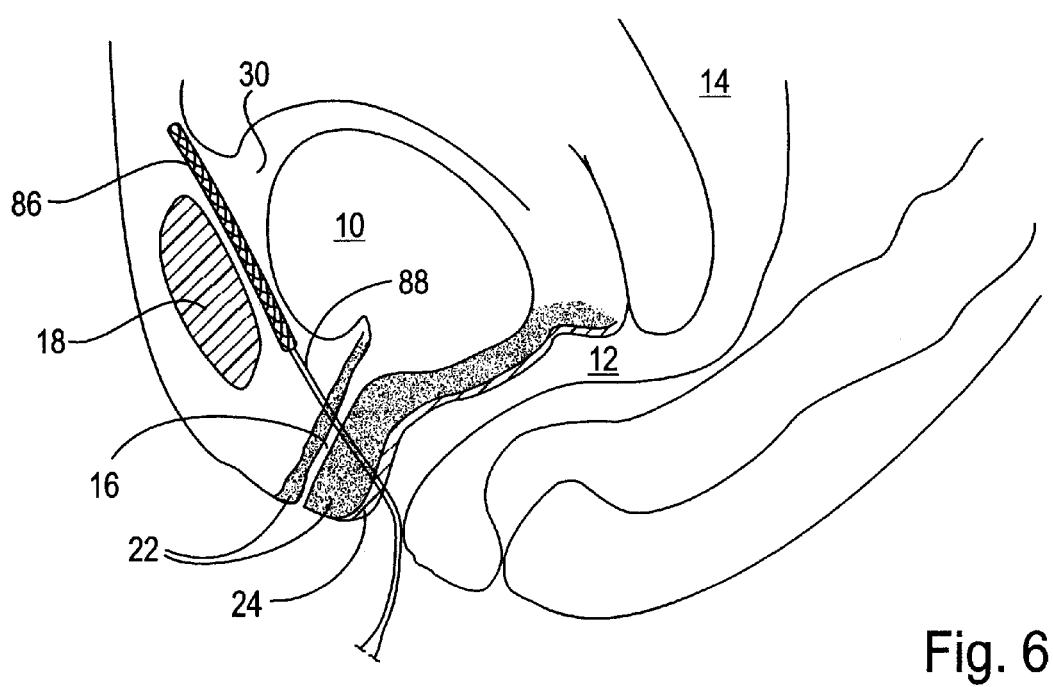
FIG. 6 is a schematic side view illustration of an anchor patch positioned so that at least a portion of the anchor patch is within the space of Retzius and sutures are positioned within the passageway exiting through the vaginal wall.

As shown in FIG. 5, the dilator 66 is then exchanged with a delivery catheter 80. The delivery catheter 80 is used to place at least a portion of a urethral support 84 within the space of Retzius 30. The urethral support 84 includes a number of embodiments which support the urethra 16 to treat urinary incontinence. In one embodiment the urethral support 84 comprises an anchor patch 86, as shown in FIG. 6. The anchor patch 86 may be comprised of a flexible, porous material having at least one side with a frictional surface. Such a frictional surface may prevent slippage of the anchor patch 86 between tissue layers during initial placement of the patch 86 and during the period of tissue ingrowth following implantation. Typical anchor patches 86 are rectangular in shape and have dimensions of approximately 1 cm in width and 16 cm in length. FIG. 6 illustrates such an anchor patch 86 deployed from the delivery catheter 80 wherein at least a portion of the anchor patch 86 is within the space of Retzius 30. In addition, the anchor patch 86 may have sutures 88 attached thereon. Typically the sutures 88 are attached to one end of the anchor patch 86 and are positioned in the passageway so that their free ends exit through the vaginal wall 26, as shown.

Figure 7:
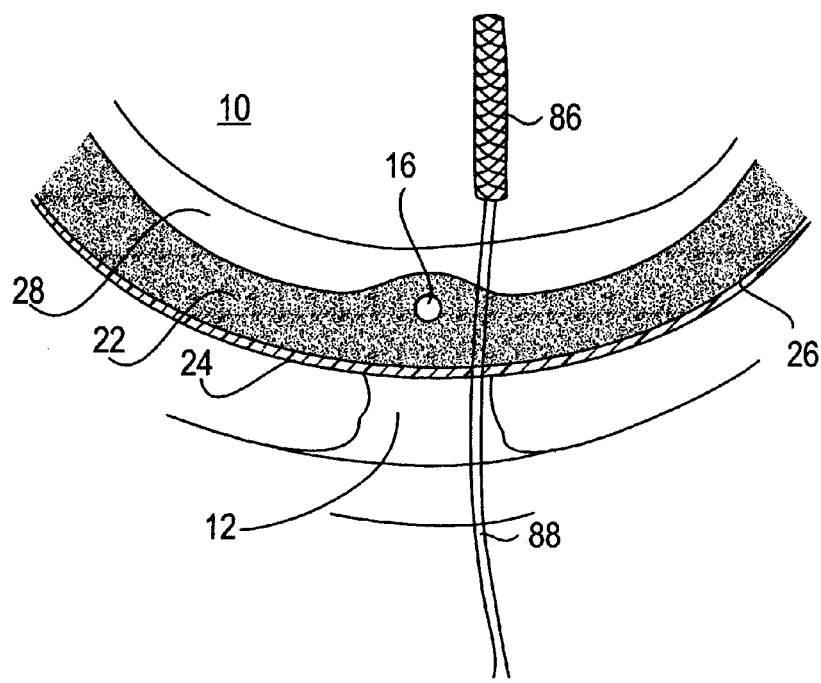
FIG. 7 is a front view schematic illustration of a positioned anchor patch as in FIG. 6.
Figure 8:
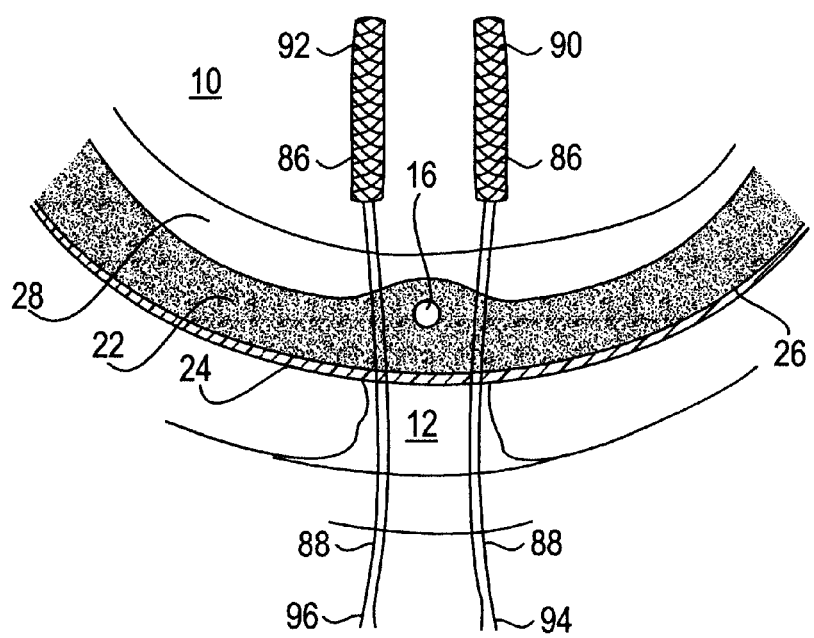
FIG. 8 illustrates the positioning of a second anchor patch on the opposite side of the urethra from the first anchor patch.

FIG. 7 provides a front view of the deployed anchor patch 86 of FIG. 6. As shown, the anchor patch 86 is positioned above the urethra 16 and the sutures 88 are positioned along a passageway which passes to one side of the urethra 16 and exits below the urethra 16 through the vaginal wall 26. This anchor patch 86 may be referred to as a first anchor patch 90. Referring now to FIG. 8, the methods depicted in FIGS. 1–7 may then be repeated on the opposite side of the urethra 16 to position another anchor patch 86 which may be referred to as a second anchor patch 92. Thus, the first and second anchor patches 90, 92 are positioned so that a portion of each patch is within the space of Retzius 30 and that they are placed approximately 2–6 cm apart to straddle the urethra 16. Likewise, first sutures 94 attached to the first anchor patch 90 and second sutures 96 attached to the second anchor patch 92 are positioned within the formed passageways so that they both exit through the vaginal wall 26 as shown.

Figure 9:
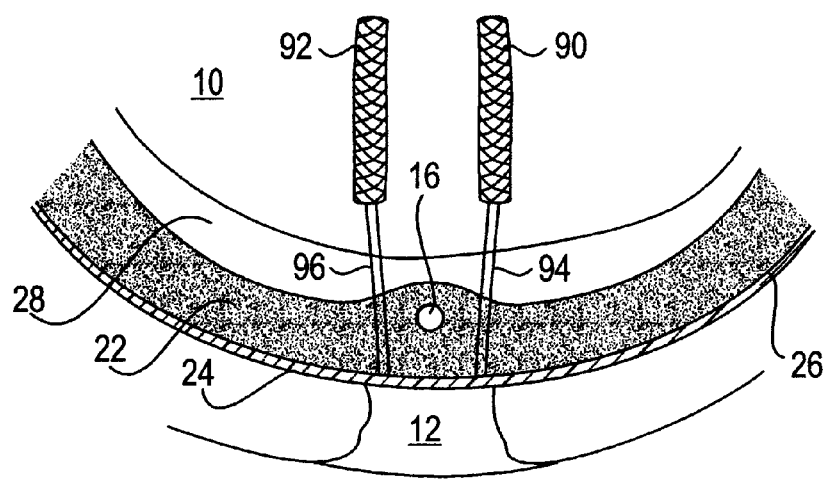
FIG. 9 illustrates one embodiment of supporting the urethra with the anchor patches wherein the anchor patches are sutured to the vaginal wall.

The first anchor patch 90 and the second anchor patch 92 are then used to provide structural support for the urethra in treating urinary incontinence. This may be achieved by a number of methods. For example, as shown in FIG. 9, the first suture 94 and the second suture 96 may each be attached to the vaginal wall 26 below the urethra 16. Such attachment may comprise attaching the sutures 94, 96 to the endopelvic fascia 22 and covering the sutures 94, 96 with the mucosal layer 24. Tension may be applied one or both patches 90, 92 by shortening the sutures 94, 96. This in turn provides various levels of support for the urethra 16, the more tension that is applied the stronger the support.

Figure 10:
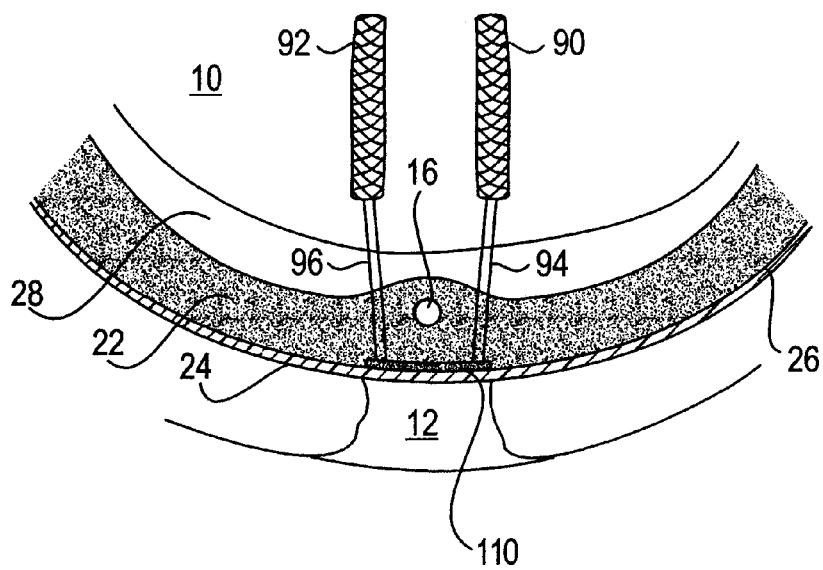
FIG. 10 illustrates an embodiment of supporting the urethra by positioning a band under the urethra and attaching the sutures from the first and second anchor patches to the band.

Alternatively, the urethra 16 may be supported by positioning a band 110 under the urethra 16, for example as shown in FIG. 10. Here, the band 110 is attached to the first sutures 94 at one of its ends and the second sutures 96 at its opposite end. However, it may be appreciated that the sutures 94, 96 may be attached to the band 110 at any locations along the band 110. Typically the band 110 is positioned within the vaginal wall 26 between the endopelvic fascia 22 and the mucosal layer 24. For example, the band 110 may be tunneled between the layers 22, 24 or the mucosal layer 24 may be peeled back for placement of the band 110 against the endopelvic fascia 22 wherein the mucosal layer 24 is then laid over the band 110. Again, by applying tension to one or both anchor patches 90, 92, the urethra 16 is structurally supported by the uplifted band 110.

Figure 11:
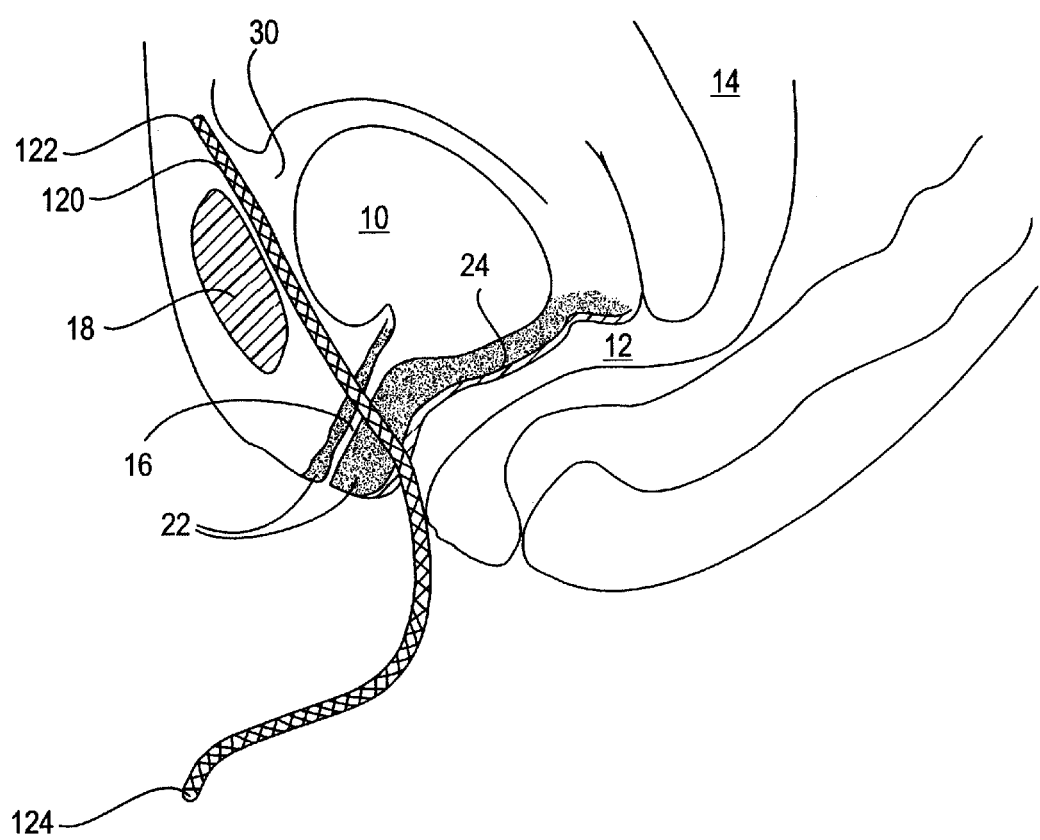
FIG. 11 is a schematic side view illustration of a sling positioned so that its first end is within the space of Retzius and its second end exits through the vaginal wall.
Figure 12:
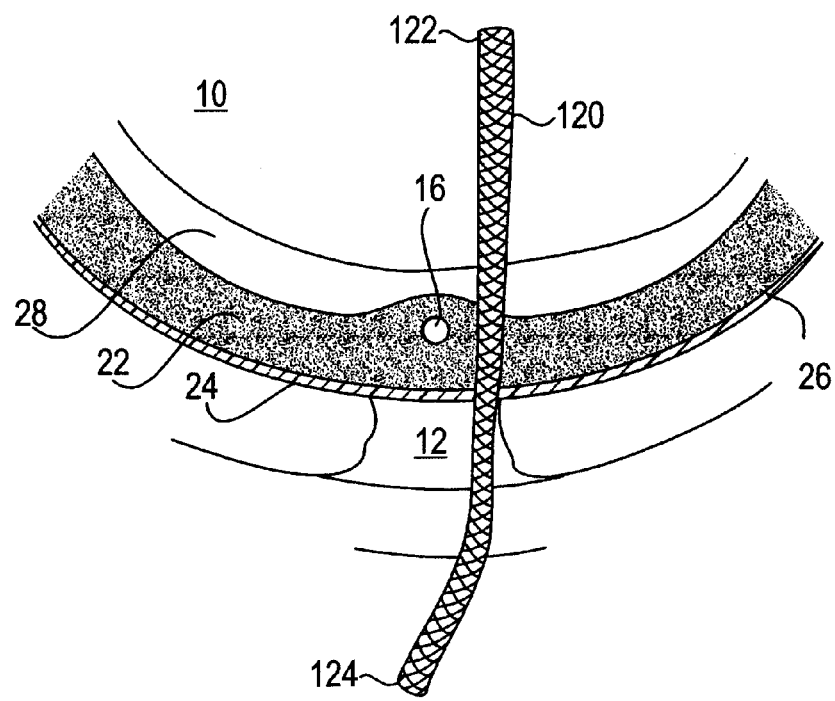
FIG. 12 is a schematic front view illustration of the sling positioned as in FIG. 11.
Figure 13:
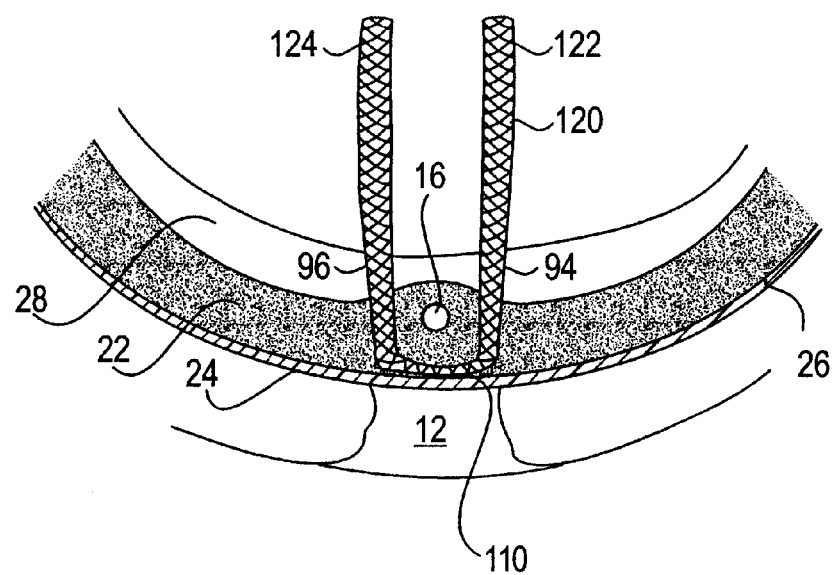
FIG. 13 illustrates the positioning of the second end of the sling within the space of Retzius so that the sling forms a loop under the urethra.

In another embodiment, shown in FIGS. 11–13, the urethral support 84 comprises a sling 120 which is used to form a loop under the urethra 16 for support. Similar to the anchor patch 86, the sling 120 may be comprised of a flexible, porous material having at least one side with a frictional surface. Again, such a frictional surface may prevent slippage of the sling 120 between tissue layers during initial placement of the sling 120 and during the period of tissue ingrowth following implantation. Typical slings 120 are rectangular in shape and have dimensions of approximately 1 cm in width and 15 cm in length. Thus, such slings 120 may have a first end 122 and a second end 124 as shown.

Positioning of such a sling 120 may be similar to positioning a first and second anchor patch 90, 92 as described above. In this manner, a passageway on one side of the urethra 16 may be formed according to the methods previously illustrated in FIGS. 1–5. As shown in FIG. 5, the urethral support 84 is deployed from a delivery catheter 80 into the space of Retzius 30. Referring now to FIG. 11, the urethral support 84, in this case the sling 120, is deployed so that at least a portion of the first end 122 is positioned within the space of Retzius 30 and the sling 120 lies in the passageway extending from the space of Retzius 30 through the vaginal wall 26 and out of the vagina 12 opening wherein the second end 124 lies outside of the body. FIG. 12 illustrates a front view of the sling 120 as positioned in FIG. 11. As shown, the sling 120 is positioned to one side of the urethra 16. At this point a second passageway is created through the vaginal wall and body tissue to a second location within the space of Retzius 30. This may again be achieved in a manner set forth in FIGS. 1–5. The second end 124 is then deployed within the space of Retzius 30 approximately 2–6 centimeters from the first end 122. As shown in FIG. 13, the sling 120 forms a loop under the urethra 16. Tension may be applied to the first and/or second ends 122, 124 by adjusting the position of the ends within the space of Retzius 30 or by shortening the length of the sling 120. In either case, upward force may be applied to the urethra 16 for structural support. As shown, the sling 120 is typically placed within the vaginal wall 26, between the endopelvic fascia 22 and the mucosal layer 24. In some cases, the sling 120 is tunneled between the layers 22, 24 or the mucosal layer 24 may be peeled back for placement of the sling 120 against the endopelvic fascia 22 wherein the mucosal layer 24 is then laid over the sling 120.

The frictional surfaces of the anchor patches or the sling assist in holding the support in place during tensioning. The support is then left in place as a long-term or short-term implant. Tissue ingrowth into the support occurs over the following 3–6 weeks to more securely hold the support in place.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method for supporting a urethra in a body to treat urinary incontinence comprising the steps of:
    providing a urethral support having a first end and a second end;
    positioning the urethral support so that it forms a loop under the urethra wherein the first end and the second end are disposed within a space of Retzius, wherein the positioning step further comprises placing at least a portion of the urethral support between an endopelvic fascia layer and a mucosal layer under the urethra; and
    leaving the urethral support implanted in the body so that the first end and second end remain within the body.

2. A method as in claim 1, further comprising creating a passageway through which at least a portion of the urethral support is positioned in the positioning step.

3. A method as in claim 2, wherein the step of creating a passageway includes penetrating through a vaginal wall and body tissue to a location within the space of Retzius.

4. A method as in claim 3, wherein the penetrating step comprises inserting a penetration device through the vaginal wall and body tissue.

5. A method as in claim 4, wherein the penetration device comprises a Veress-style needle.

6. A method as in claim 4, wherein inserting the penetration device further comprises contacting a depth stop against the vaginal wall.

7. A method as in claim 4, wherein a sheath is mounted on the penetration device and further comprising removing the penetration device leaving the sheath behind in the passageway.

8. A method as in claim 7, further comprising inserting a blunt dilator into the sheath.

9. A method as in claim 8, further comprising inserting a delivery catheter into the sheath.

10. A method as in claim 9, further comprising deploying the first or second end of the urethral support from the delivery catheter within the space of Retzius.

11. A method as in claim 3, wherein inserting the penetration device further comprises contacting a depth stop against the vaginal wall.

12. A method of minimally invasively positioning a sling for support of a urethra in a body to treat urinary incontinence comprising the steps of:
    creating a first passageway through a vaginal wall and body tissue to a first location within a space of Retzius;
    passing a first end of a sling through the first passageway;
    positioning the first end within the space of Retzius
    positioning the sling so that it forms a loop, under the urethra between an endopelvic fascia layer and a mucosal layer, and supports the urethra; and
    leaving the first end implanted within the body.

13. A method as in claim 12, further comprising:
    creating a second passageway through the vaginal wall and body tissue to a second location within the space of Retzius;
    passing a second end of the sling through the second passageway; and
    positioning the second end within the space of Retzius.

14. A method as in claim 12, further comprising adjusting the position of the sling to apply tension on the first or second ends.

15. A method as in claim 12, further comprising applying tension to the first or second ends to support the urethra.

16. A method for supporting a urethra in a body to treat urinary incontinence comprising the steps of:
    providing a urethral support having a first end and a second end;
    positioning the urethral support so that it forms a loop under the urethra wherein the first end and the second end are disposed within a space of Retzius;
    creating a passageway through which at least a portion of the urethral support is positioned in the positioning step by penetrating through a vaginal wall and body tissue to a location within the space of Retzius, wherein penetrating comprises inserting a penetration device through the vaginal wall and body tissue, and wherein a sheath is mounted on the penetration device;

removing the penetration device leaving the sheath behind in the passageway; and leaving the urethral support implanted in the body.

17. A method as in claim 16, further comprising inserting a blunt dilator into the sheath.

18. A method as in claim 17, further comprising inserting a delivery catheter into the sheath.

19. A method as in claim 18, further comprising deploying the first or second end of the urethral support from the delivery catheter within the space of Retzius.

20. A method as in claim 16, wherein the penetration device comprises a Veress-style needle.

21. A method as in claim 16, wherein inserting the penetration device further comprises contacting a depth stop against the vaginal wall.

22. A method for supporting a urethra in a body to treat urinary incontinence comprising the steps of:

providing a urethral support having a first end and a second end;

positioning the urethral support so that it forms a loop under the urethra wherein the first end and the second end are disposed within a space of Retzius;

creating a passageway through which at least a portion of the urethral support is positioned in the positioning step by penetrating through a vaginal wall and body tissue to a location within the space of Retzius, wherein penetrating comprises inserting a penetration device through the vaginal wall and body tissue, and wherein a sheath is mounted on the penetration device;

removing the penetration device leaving the sheath behind in the passageway; and leaving the urethral support implanted in the body so that the first end and second end remain within the body.

23. A method as in claim 22, further comprising inserting a blunt dilator into the sheath.

24. A method as in claim 23, further comprising inserting a delivery catheter into the sheath.

25. A method as in claim 24, further comprising deploying the first or second end of the urethral support from the delivery catheter within the space of Retzius.

26. A method as in claim 22, wherein the penetration device comprises a Veress-style needle.

* * * * *